US00PP09547P

United States Patent [19]

Zary

[11] Patent Number: Plant 9,547

[45] Date of Patent: May 14, 1996

[54] HYBRID TEA ROSE PLANT NAMED 'JACALTO'

[75] Inventor: Keith W. Zary, Thousand Oaks, Calif.

[73] Assignee: Bear Creek Gardens, Inc., Medford, Oreg.

[21] Appl. No.: 491,144

[22] Filed: Jun. 16, 1995

[51] Int. Cl.[6] ..... A01H 5/00

[52] U.S. Cl. ..... Plt./20

[58] Field of Search ..... Plt./20, 21

*Primary Examiner*—Howard J. Locker

*Attorney, Agent, or Firm*—Klarquist Sparkman Campbell Leigh & Whinston

[57] ABSTRACT

A new rose variety of the hybrid tea class having exceptionally long stems; long, bright red buds; large, bright red flowers; and a vigorous, upright habit of growth.

1 Drawing Sheet

The present invention relates to a new and distinct variety of rose plant of the hybrid tea class which was originated by me by crossing an unnamed seedling (not patented) with another unnamed seedling (not patented).

The primary objective of this breeding was to produce a new rose variety having the vigor, long stems and excellent bud and flower form of the female, combined with the excellent flower color, large petals and long stems of the male parent. The objective was substantially achieved, along with other desirable improvements, as evidenced by the following unique combination of characteristics that are outstanding in the new variety and that distinguish it from its parents, as well as from all other varieties of which I am aware:

1. Exceptionally long, straight stems.
2. Excellent bright red flower color.
3. Long flower buds.
4. Large open flower.
5. Vigorous, upright habit of growth.

Asexual reproduction of this new variety by budding, as performed at Wasco, Calif., shows that the foregoing and all other characteristics and distinctions from true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicted.

Parentage:

*Seed parent.*—Unnamed seedling (not patented).

*Pollen parent.13* Unnamed seedling (not patented).

Classification:

*Botanical.*—Rosa hybrida.

*Commercial.*—Hybrid tea.

FLOWER

Observations made from specimens grown in a greenhouse environment at Somis, Calif.

Blooming habit: Continuous.

Bud:

*Size.*—*b* 1¾ to 2 inches long when the petals start to unfurl.

*Form.*—The bud form is long and pointed ovoid.

*Color.*—When sepals first divide, bud color is Red Group 46B. When half blown, the upper sides of the petals are Red Group 46B; and the lower sides of the petals are Red Group 46B.

*Sepals.*—Color: Green Group 138C. Surface texture: Covered in fine hairs. There are three normally appendaged sepals. There are two unappendaged sepals with hairy edges.

*Receptacle.*—Color: Green Group 138B. Shape: Funnel. Size: Medium (⅜"×⅜"). Surface: Smooth.

*Peduncle.*—Length: Long (4½"–5"). Surface: Smooth. Color: Light Green. Strength: Stiff and erect.

Bloom:

*Size.*—Large. Average open size is 5 inches.

*Borne.*—Singly.

*Stems.*—Very long. Average length is about 26"–30".

*Form.*—When first open: High centered. Permanence: Retains its form to the end and outer petals curl back.

*Petalage.*—Number of petals under normal conditions: 30–35.

*Color.*—The upper side of the petals is Red Group 46B. The reverse side of the petals is Red Group 46B. The base of each petal has a small white half-moon (¼"×¼") at its point of attachment. The major color on the upper side is Red Group 46B.

*Variegations.*—None.

*Discoloration.*—The general tonality at the end of the first day: No change. At the end of the third day: No change. By day 8 or 9, in the vase there is a general bluing of the flower.

*Fragrance.*—Moderate.

Petals:

*Texture.*—Thick.

*Shape.*—Round.

*Form.*—Tips slightly recurved and moderately quilled.

*Arrangement.*—Imbricated, with few petaloids in the center.

*Persistence.*—Drop off cleanly.

*Lastingness.*—On the plant: Long, 7–8 days. As a cut flower: Long, 9–10 days.

Reproductive parts:

*Anthers.*—Size: Medium. Quantity: Many. Color: Yellow. Arrangement: Regular around styles.

*Filaments.*—Color: Yellow.

*Pollen.*—Color: Lemon Yellow.

*Styles.*—Color: Yellow.

*Stigmas.*—Color: Greenish-white.

Form: Bush.

Growth: Very vigorous, upright and branching. Height in the greenhouse after one year will exceed 10 feet tall by 4 feet wide. Plant produces 120 to 130 stems per square meter of greenhouse.

Foliage: Number of leaflets on normal mid-stem leaves.

*Size.*—Large, 6"×4".

*Quantity.*—Normal.

*Color.*—New foliage: Greyed Purple Group 185B. Old foliage: Upper surface: Green Group 139A; Lower surface: Green Group 139C.

Leaflets:

*Shape.*—Pointed oval.

*Texture.*—Upper side: Leathery.

*Edge.*—Serrated.

*Serration.*—Single.

*Petiole rachis.*—Color: Green.

*Petiole underside.*—Smooth, with occasional prickles.

*Stipules.*—Short (5/16"); serrated.

*Disease resistance.*—Susceptible to mildew under normal greenhouse growing conditions at Somis, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium (5/16"), hooked downward.

*Color when young.*—Red.

Small prickles:

*Quantity.*—On main stalks: None. On laterals: None.

I claim:

1. A new and distinct variety of rose plant of the hybrid tea class, substantially as herein shown and described, characterized particularly as to novelty by the unique combination of its exceptionally long stems; its long, bright red buds; its large, bright red flowers; and its vigorous, upright habit of growth.

* * * * *

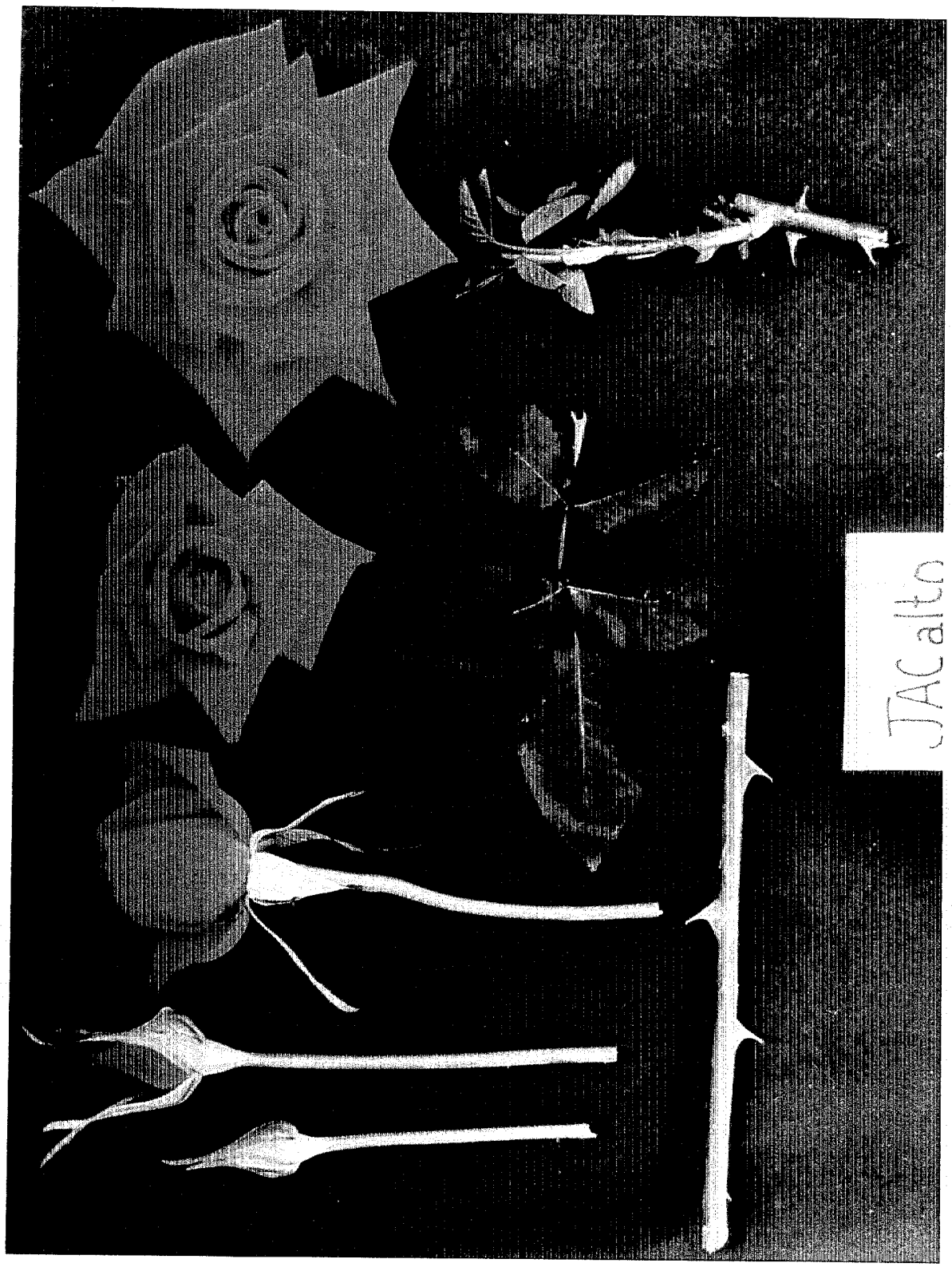
JACalto

UNITED STATES PATENT AND TRADEMARK OFFICE

CERTIFICATE OF CORRECTION

PATENT NO. : PP 9,547

DATED : May 14, 1996

INVENTOR(S) : Keith W. Zary

It is certified that error appears in the above-indentified patent and that said Letters Patent is hereby corrected as shown below:

Column 1, line 22, "distinctions from true" should read --distinctions come true--.

Column 1, line 47, "Size.—b 1 3/4 " should read --Size.—1 3/4 --.

Signed and Sealed this

Eighth Day of October, 1996

Bruce Lehman

*Attest:*

BRUCE LEHMAN

*Attesting Officer*

*Commissioner of Patents and Trademarks*